United States Patent [19]

Frankel et al.

[11] Patent Number: 5,549,609
[45] Date of Patent: Aug. 27, 1996

[54] BONE FIXATION FOR FRACTURES OF THE UPPER ULNA

[75] Inventors: Victor H. Frankel; Frederick J. Kummer, both of New York, N.Y.

[73] Assignee: Hospital for Joint Diseases, New York, N.Y.

[21] Appl. No.: 317,287

[22] Filed: Oct. 3, 1994

Related U.S. Application Data

[63] Continuation of Ser. No. 116,700, Sep. 7, 1993, abandoned.
[51] Int. Cl.⁶ .................................................. A61B 17/72
[52] U.S. Cl. .................................................. 606/64
[58] Field of Search ........................... 606/60, 62, 64, 606/65, 66, 67, 68, 72, 75, 105

[56] References Cited

U.S. PATENT DOCUMENTS

| | | | |
|---|---|---|---|
| 2,614,559 | 10/1952 | Livingston . | |
| 2,696,817 | 12/1954 | Prevo . | |
| 2,821,979 | 2/1958 | Cameron | 606/64 |
| 2,952,254 | 9/1960 | Keating | 606/75 |
| 3,763,855 | 10/1973 | McAtee . | |
| 3,990,438 | 11/1976 | Pritchard . | |
| 4,212,294 | 7/1980 | Murphy . | |
| 4,858,602 | 8/1989 | Seider et al. | 606/62 |
| 4,913,137 | 4/1990 | Azer et al. | 606/96 |
| 4,997,433 | 3/1991 | Goble et al. | 606/62 |
| 5,013,316 | 5/1991 | Goble et al. | 606/72 |
| 5,053,035 | 10/1991 | McLaren . | |
| 5,057,110 | 10/1991 | Kranz et al. . | |

*Primary Examiner*—Tamara L. Graysay
*Attorney, Agent, or Firm*—Stephen E. Feldman

[57] ABSTRACT

A bone fixation assembly for fracture(s) of the upper ulna, the ulna having an olecranon and a proximate end, comprising a elongated medullary pin and a head member. The elongated medullary pin has a longitudinal axis and distal and proximal ends and at least one aperture at its distal end for transverse locking screw(s). The head member is disposed at the proximal end of the pin for transmitting force to the olecranon along the longitudinal axis of the pin as the head member is tightened. The head member comprising at least one inwardly extending, projecting, pointed portion.

6 Claims, 1 Drawing Sheet

BONE FIXATION FOR FRACTURES OF THE UPPER ULNA

This application is a continuation of application Ser. No. 08/116,700 filed Sept. 7, 1993 now abandoned.

FIELD OF THE INVENTION

This invention relates to-the field of bone fixation assemblies and in particular to a bone fixation assembly for fractures of the proximal ulna, one of the forearm bones.

DESCRIPTION OF THE PRIOR ART

In order to set a broken bone and to properly maintain the bone fragments in a fixed condition during the period of healing, it is especially desirable to keep the bone fragments under compression. Such compression increases the rate of healing. Additionally, relative rotation of the bone fragments of the bone must be prevented during the healing period.

If the ulna is broken close to its proximal end, the triceps muscles tend to move the bone fragments away from the distal portion of the bone and it is difficult to properly set the bone fragments in their proper position for healing, and thus restore normal elbow function.

An intramedullary bar used in the healing of fractured bones, is disclosed by Livingston in U.S. Pat. No. 2,614,559. The intramedullary bar is placed in the medullary cavity of a bone, and held therein in spaced relationship to the bone by means of screws passing through the bone and through any substantial fragments thereof. This permits the broken bone and/or fragments thereof, to be held in their correct positions while the healing process proceeds to completion. The bar is provided with a plurality of spaced holes, and companionate screws are provided for the holes, which screws have a bore diameter with an outer diameter adapted to pass through the holes.

An assembly for fixation of bone fractures of the ulna near the elbow joint is disclosed by McAtee in U.S. Pat. No. 3,763,855. This device is used for the positive fixation of fractures of the ulna, one of the forearm bones. One element of the assembly is secured to the distal part of the ulna, and another threaded element is independently tightened up to impact the bone fragments. The first element is a metal element or unit inserted from the side through the hard outer part of the forearm bone, below the break. This metal element, referred to as the cortical fixation unit, extends into the soft center channel of the bone and has a transverse threaded hole near its end, opening to the center channel of the bone. The other element referred to as a "pin" is a flexible bolt or pin formed of a threaded, stiff, wire having a bolt head at one end.

This flexible pin is pushed through a drilled hole in the elbow fragment of the bone, down the bone channel and engages with the threaded hole at the end of the cortical fixation unit. By tightening the bolt head on the flexible pin, the elbow fragment is positively set in its proper position in engagement with the remaining distal portion of the ulna. The above described procedure is difficult to accomplish as it is difficult to thread the threaded pin through the cortical fixation unit. Furthermore rotation control of the proximate bone fragment is not provided.

A bone fracture fixation and compression apparatus, is disclosed by Pritchard in U.S. Pat. No. 3,990,438. It comprises a lag screw member and a compression screw for maintaining a broken bone fragment and the principal bone. The lag screw member includes a first end with cutting threads for anchoring the lag screw member within the principal bone. The other end of the lag screw member includes a threaded socket for receiving the threaded portion of the bone compression screw after it passes through the bone fragment. The broad slotted head of the compression screw holds the bone fragment under pressure against the principal bone when the compression screw is rotated into the socket of the lag screw member. However, rotation control of the proximate bone fragment is not provided.

Another orthopedic fracture fixation device, is disclosed by Murphy in U.S. Pat. No. 4,212,294. This orthopedic fixation device for fixation of fractures of the proximal end of the ulna comprises a first fixation member or rod and a second fixation member or pin. The first fixation member has an enlarged head and an elongated body having a threaded aperture formed in the mid-portion thereof and a threaded outer portion. The second fixation member comprises an elongated pin having a smooth tapered tip at one end thereof and a head having a groove formed on the outer surface thereof at the opposite end thereof, specifically configured to provide a three point fixation. When installed, the rod goes through the pin, however, it is difficult to thread the pin through the rod. Also rotation control of the proximate bone fragment is not provided.

An object of the present invention is to provide an improved bone fixation for fractures of the ulna which provides rotation control of the proximate bone fragment.

Another object of the present invention is to provide an improved bone fixation assembly for fractures of the upper ulna comprising a pin, which when installed in the upper ulna does not require a cortical screw for the proximate end of the pin.

A still further object of the present invention is to provide an improved bone fixation assembly for fractures of the upper ulna having a staple like head which prevents relative rotation of the bone fragments of the broken upper ulna bone during the healing period.

An additional object of the present invention is to provide a bone fixation assembly for fractures of the upper ulna, that enhances the compression between the fractured surfaces to improve the rigidity of fracture fixation thereby improving bone healing.

SUMMARY OF THE INVENTION

The present invention, in its broadest aspect, is directed to a bone fixation assembly for fracture(s) of the upper ulna, the ulna having an olecranon and a proximate end, comprising a elongated medullary pin and a head means. The elongated medullary pin has a longitudinal axis and distal and proximal ends and at least one aperture at its distal end. The head means is disposed at the proximal end of the pin for transmitting force to the olecranon along the longitudinal axis of the pin as the head means is tightened. The head means comprises at least one inwardly extending, projecting, pointed portion.

The present invention in its narrowest aspect of the preferred embodiment, is directed to a bone fixation assembly for fracture(s) of the upper ulna, said ulna having an olecranon and a proximate end, comprising a elongated medullary pin and a head means. The elongated medullary pin has a longitudinal axis and distal and proximal ends and has aperture(s) disposed only at its distal end. The head means is disposed at the proximal end of said pin for transmitting force to the olecranon along the longitudinal axis of the pin as said head means is tightened, and comprises a U-shaped member and a screw. The U-shaped member, for holding the proximate end of said pin in place at the proximate end of said ulna comprises, two inwardly extending, projecting, pointed portions, a sleeve portion disposed around the proximal end of the pin, and an aperture having a longitudinal axis which coincides with the longitudinal axis of the pin. The screw is disposed within the aperture of said U-shaped member for compressing said fracture(s). The sleeve member and the proximate end of the pin are adapted to prevent rotation of the head means within the upper ulna.

BRIEF DESCRIPTION OF THE DRAWINGS

The above and other objects and advantages and novel features of the present invention will become apparent from the following detailed description of the invention illustrated in the accompanying drawings, in which.

In the drawings like reference numerals are used to indicate like elements.

DETAILED DESCRIPTION OF THE INVENTION

Figure 1:
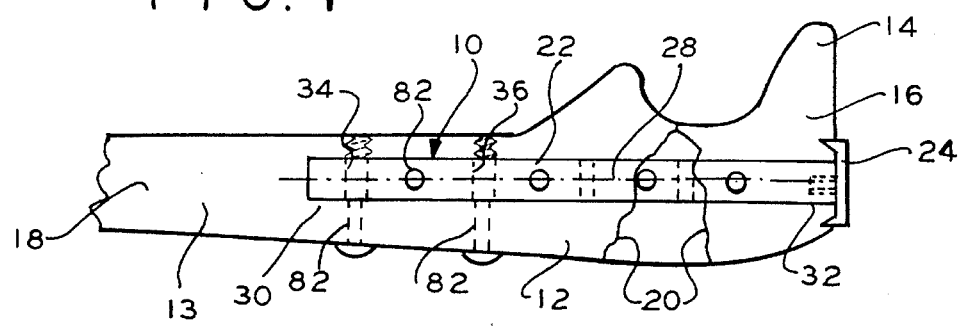
FIG. 1 is a simplified view of the bone fixation assembly shown installed in a fractured upper ulna.
Figure 2A:
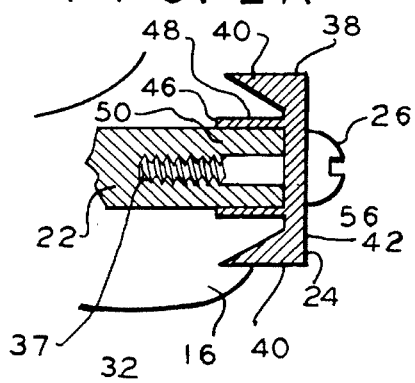
FIG. 2A is a simplified, cross-sectional, plan view of the preferred embodiment of the bone fixation assembly shown installed in a proximate portion of the fractured upper ulna.
Figure 2B:
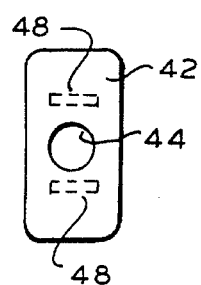
FIG. 2B is a simplified top view of the staple member of the bone fixation assembly of FIG. 2A.

Referring to FIG. 1, the present invention generally relates to an orthopedic fixation assembly and method for fixation of bone fractures generally indicated as 10. As more fully described hereinafter, the orthopedic assembly 10 specifically relates to a bone fixation assembly for fracture(s) of the upper ulna generally indicated as 12. The upper ulna 12 has an olecranon or elbow protuberance 14, a shaft 13 having a medullary canal, and proximate and distal ends, 16 and 18, respectively, and fracture or break lines 20.

Referring now to FIGS. 1 and 2, the orthopedic fixation assembly 10 comprises a rigid, elongated, medullary pin 22, a head means 24, and fastening members 26. The pin 22 is shown as a solid member having a longitudinal axis 28, distal and proximal ends, 30 and 32, respectively, a plurality of spaced apart unthreaded apertures 34 and 36, and a longitudinally extending, threaded, aperture 37 at the proximal end 32. However, the pin 22 could be convoluted to slip over a guide pin. The head means 24 is disposed at the proximal end 32 of the pin 22 and functions to transmit force to the olecranon 14 along the longitudinal axis 28 of the pin 22 as it is tightened (discussed infra). The head means 24 comprises a generally U-shaped member 38 for holding the proximate end 32 of the pin 22 in place at the proximate end 16 of the ulna 12. The U-shaped member or staple member 38 comprises a pair of opposed, inwardly extending, pointed, projecting or arm portions 40, connected by a rigid bridging or central portion 42 which has a central aperture 44 having a longitudinal axis 46 which coincides with the longitudinal axis 28 of the pin. The arm portions 40 are adapted to penetrate the proximate end 16 of the upper ulna 12. In the preferred embodiment shown in FIG.2, the head means 24 is separate from the pin 22 and comprises the U-shaped member 38 having an integral, two leg sleeve portion 48 disposed around the upper portion 50 of the proximal end 32 of the pin 22 and a screw 56 (only the head of which is shown) which engages the upper portion of the threaded recess 37 formed in the upper portion 50 of the proximal end 32 of the pin 32. Alternately, the integral sleeve portion 48 can be in the form of a square sleeve. The screw 56 is disposed within the central aperture 44 of the U-shaped member 38 and engages the upper portions 50 of the threaded recess 37. The sleeve portion 48 and the outside surface of the upper portion 50 of the pin 22 are keyed to each other to prevent the staple member 38 from rotating. In the embodiment shown in FIG. 3 the U-shaped member 38 is integral with the upper portion 50 of proximate end 32 of the pin 22; a shorter longitudinally extending, threaded, aperture 37 is formed at the proximal end 32 of the pin 22.

In the preferred embodiment of the head means 24 shown in FIGS. 2 the arm portions 40 of the staple member 38 are spaced apart approximately 15 mm and has a preferred prong height of between 2–3 mm, a preferred thickness of between 1–2 mm, and is initially laterally disposed away from the sleeve 48 a distance of between 5–10 mm. The pin 22 is preferably 15 cm long with a diameter of between about 6–8 mm. The diameter of the apertures 34 and 36 are about 3.5 mm.

Figure 4:
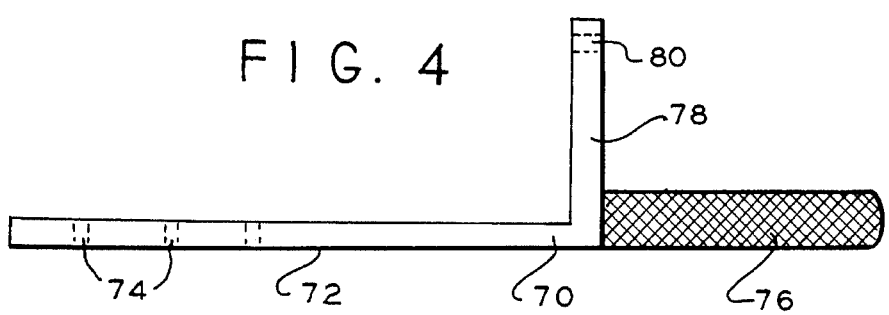
FIG. 4 is a simplified plan view of an alignment fixture used in installing the bone fixation assembly within the upper ulna.

In order to lock the orthopedic assembly 10 to the upper ulna 12, the alignment fixture 70 shown in FIG. 4 must be utilized. The alignment fixture 70 comprises an elongated, first aligning portion 72 having a plurality of spaced apart apertures 74, a handle 76 affixed to said first aligning portion 72, and a laterally extending, second aligning portion 78 having a single aperture 80 therein. The aperture 74 in the first aligning portion 72 are spaced apart the same distance that the two apertures 34 and 36 in the pin 22 are spaced apart.

Another embodiment of the alignment fixture 70 would include a plurality of spaced apart third aligning portions to align the transverse holes 74 (discussed infra). These third aligning portions would be offset laterally and extend from and be affixed to the first aligning portion 72 between apertures 74 and be disposed parallel to the plane of both the first and second aligning portions 72 and 78.

The method of installing and locking the pin 22 in the upper ulna 12 in the embodiment shown in FIG. 2 comprises the following steps:

A. After a longitudinally extending first hole and a second, wider (diameter equal to the diameter of the sleeve portion 48) hole is conventionally drilled in the upper ulna 12 using a guide wire (not shown), the pin 22 itself is disposed in the drilled hole in the ulna 12 by attaching the threaded end of an elongated installing rod (not shown) within the matching, threaded aperture 37 in the proximate end 32 of the pin 22, and then the pin 22 is forced into the aperture 37 by exerting a force on the opposite, free, end of the installing rod. After it is properly installed, the installing tool is detached from the proximate end 32 of the pin 22.

B. The second alignment portion 78 of the alignment fixture 70 is attached to the proximate end 32 of the pin 22 through the use of a threaded bolt (not shown) which is disposed through its aperture 80 and then threaded into aperture 37 of the pin 22 until the alignment fixture 70 is secured in place.

C. After the alignment fixture 70 is secured to the pin 22, the location of the distal apertures 34 and 36 are determined by viewing the upper ulna 12 through the apertures 74 of the first aligning portion 72 of the alignment fixture 70.

D. Drilling distal holes in the upper ulna 12 through the distal apertures 74 alignment fixture 70; this step is accomplished by the use of a drill or reamer.

E. Inserting locking cortical screws 82 through the drilled distal holes and distal apertures 34 and 36 in the distal end 30 of the pin 22; this is accomplished by installing the screws 82 into the reamed holes of the upper ulna 12 and the aligned distal apertures 34 and 36.

F. Detaching the alignment fixture 70 from the proximate end 32 of the pin 22.

G. Inserting the sleeve portion 48 in the second, wider, hole over the upper portion 50 of the pin 22.

H. Inserting screw 56 through the aperture 44 of the staple member 38 and into the threaded aperture 37 and turning it down so that its pointed portions 40 penetrate the proximate end 16 of the upper ulna 12 and until its central portion 42 is flush with the outside surface of its proximate end 16.

Figure 3:
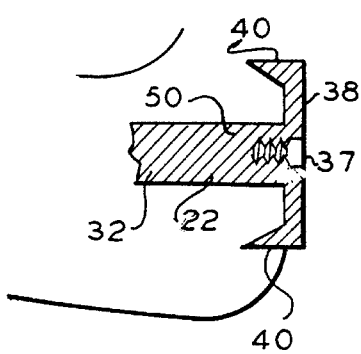
FIG. 3 is a simplified, cross-sectioned, plan view of another embodiment of the bone fixation assembly shown installed in a proximate portion of the fractured upper ulna.
Figure 2C:
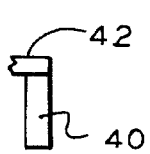
FIG. 2C is a simplified side view of one of the pointed portions of the staple member of the bone fixation assembly of FIG.2A.
Figure 2D:
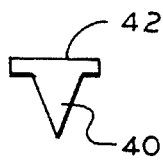
FIG. 2D is a simplified end view of one of the pointed portions of the staple member of the bone fixation assembly of FIG.2A.

The method of installing and locking the pin 22 in the upper ulna 12 in the second embodiment shown in FIG. 3 is similar to the first embodiment except that the free end of the installing rod is used to drive the pointed portions 40 of the staple member 38 into the proximate end 16 of the upper ulna 12 by exerting force or striking the free end of the installing rod with a hammer. Therefore steps G and H are eliminated.

In additional to the apertures 34 and 36, the pin 22 has a plurality of spaced apart, transverse holes 82. These holes 82 are orthogonally oriented with respect to the longitudinal axes of apertures 34 and 36. These holes 82 are used with appropriate additional screws (not shown) to secure any bone fragment which breaks off from the lateral or medial side of the fractured ulna 12.

While the invention has been shown in a preferred embodiment and in an alternative embodiment thereof, numerous changes or modifications may occur to workers in the art without departure from the spirit and scope of the invention.

Having described this invention what is sought to be protected by Letters of Patent is set forth in the following claims:

1. A bone fixation assembly for at least one fracture of an upper ulna, said ulna having an olecranon and a proximate end, comprising:
   an elongated medullary pin having a longitudinal axis and distal and proximal ends and having at least one aperature disposed only at its distal end; and
   a head means disposed at the proximal end of said pin for transmitting force to the olecranon along the longitudinal axis of said pin as said head means is tightened, comprising,
      a U-shaped member, for holding the proximate end of said pin in place at the proximate end of said ulna, the U-shaped member comprising,
         two inwardly extending, projecting, pointed portions,
         a sleeve portion disposed around the proximal end of the pin, and
         an aperture having a longitudinal axis which coincides with the longitudinal axis of said pin and
      a screw disposed within said aperture of said U-shaped member for compressing said at least one fracture, and
   said sleeve member and said proximate end of said pin are adapted to prevent rotation of said head means within said upper ulna.

2. A bone fixation assembly for fractures of an upper ulna having an olecranon, a proximate end and a shaft having a medullary canal, said medullary canal having a longitudinal axis, said bone fixation assembly comprising:
   a) an elongated medullary pin adapted to be introduced proximately into said medullary canal of said shaft, said elongated medullary pin having a longitudinal axis, a distal end and a proximal end and at least one transverse aperture at said distal end;
   b) a head means disposed at said proximal end of said pin for transmitting force to said olecranon along said longitudinal axis of said pin as said head means is tightened, said head for means contacting said medullary pin for a time period defined by the fractures healing period of upper ulna bone fragments; and
   said head means including at least one inwardly extending, projecting portion and a U-shaped member for holding said proximal end of said pin in place at a proximate end of said ulna, said U-shaped member having a sleeve portion disposed around said proximal end of said pin.

3. The bone fixation assembly as recited in claim 2, wherein said sleeve portion and said proximate end of said pin are adapted to prevent rotation of said head means within said upper ulna.

4. A bone fixation assembly as recited in claim 2 wherein said at least one transverse aperture of said elongated medullary pin is positioned only at said distal end of said elongated medullary pin.

5. A bone fixation assembly as recited in claim 2 wherein said elongated medullary pin further includes at least two spaced apart transverse apertures orthogonally oriented with respect to said longitudinal axis of said at least one transverse aperture.

6. A bone fixation assembly for fractures of an upper ulna, said upper ulna having an olecranon, a proximate end and a shaft having a medullary canal, said medullary canal having a longitudinal axis, said bone fixation assembly comprising:
   a) an elongated medullary pin adapted to be introduced proximally into said medullary canal of said shaft, said elongated medullary pin having a longitudinal axis, a distal end and a proximal end and at least one transverse aperture at said distal end;
   b) a head means disposed at said proximal end of said pin for transmitting force to said olecranon along said longitudinal axis of said pin as said head means is tightened, said head means in contact with said medullary pin for a time period defined by the fractures healing period of said upper ulna bone fragments;
   c) said head means including at least one inwardly extending, projecting pointed portion and a U-shaped member for holding said proximate end of said pin in place at said proximate end of said ulna; and,
   d) said U-shaped member has an aperture having a longitudinal axis which coincides with said longitudinal axis of said pin and said head means further includes a screw disposed within an aperture of said head means for compressing said fracture(s).

* * * * *